(12) United States Patent
Hörlle et al.

(10) Patent No.: US 8,911,437 B2
(45) Date of Patent: Dec. 16, 2014

(54) MEDICAL TECHNOLOGY DEVICE AND MEDICAL TECHNOLOGY DEVICE ARRANGEMENT

(75) Inventors: Andreas Hörlle, Berlin (DE); André Roggan, Berlin (DE); Wolfgang Kühne, Schönfliess (DE); Uwe Fischer, Berlin (DE); Timo Strauss, Berlin (DE); Stefan Schiddel, Potsdam (DE); Christopher Sprenger, Berlin (DE)

(73) Assignee: Olympus Winter & Ibe GmbH (DE)

( * ) Notice: Subject to any disclaimer, the term of this patent is extended or adjusted under 35 U.S.C. 154(b) by 223 days.

(21) Appl. No.: 13/591,385

(22) Filed: Aug. 22, 2012

(65) Prior Publication Data

US 2012/0316588 A1    Dec. 13, 2012

Related U.S. Application Data

(62) Division of application No. 12/537,319, filed on Aug. 7, 2009.

(30) Foreign Application Priority Data

Sep. 15, 2008    (DE) .................. 10 2008 047 339

(51) Int. Cl.
*A61B 18/10* (2006.01)
*H01R 13/44* (2006.01)
*H01R 13/52* (2006.01)
*H01R 13/74* (2006.01)

(52) U.S. Cl.
CPC ........ *H01R 13/5213* (2013.01); *H01R 13/5224* (2013.01); *H01R 13/74* (2013.01); *Y10S 439/909* (2013.01)
USPC .............. 606/34; 439/136; 439/139; 439/909

(58) Field of Classification Search
USPC ......... 439/135–136, 138–140, 190, 199, 271, 439/909, 700; 606/34, 39, 40
See application file for complete search history.

(56) References Cited

U.S. PATENT DOCUMENTS

| 3,794,956 A | 2/1974 | Dubreuil |
| 4,091,231 A | 5/1978 | Sotolongo |

(Continued)

FOREIGN PATENT DOCUMENTS

| DE | 37 20 099 | 12/1987 |
| DE | 196 54 206 | 7/1997 |

(Continued)

OTHER PUBLICATIONS

German Search Report issued in corresponding German Application No. 10 2008 047 339.1.

(Continued)

*Primary Examiner* — Jaymi Della
(74) *Attorney, Agent, or Firm* — Ostrolenk Faber LLP

(57) ABSTRACT

The invention concerns a medical technology device for treatment of the human or animal body, comprising at least one electrical plug connector which is adapted to be connected to a complementary counterpart plug connector of a further medical technology device and which in an active position is arranged projecting upwardly at the top side of the device. To provide a medical technology device which can be used both as an individual device and also in conjunction with a second device as a device arrangement and which in that respect satisfies existing safety and aesthetic demands, it is provided in accordance with the invention that the plug connector is adapted to be movable from the active position into a passive position, wherein in the passive position the plug connector is removed from the top side of the device and the top side is closed in substantially fluid-tight relationship.

6 Claims, 8 Drawing Sheets

(56) References Cited

U.S. PATENT DOCUMENTS

| | | |
|---|---|---|
| 4,718,858 A | 1/1988 | Godfrey et al. |
| 4,860,745 A | 8/1989 | Farin et al. |
| 5,023,396 A | 6/1991 | Bartee |
| 5,122,138 A | 6/1992 | Manwaring |
| 5,169,398 A | 12/1992 | Glaros |
| 5,244,462 A | 9/1993 | Delahuerga et al. |
| 5,267,997 A | 12/1993 | Farin et al. |
| 5,275,597 A | 1/1994 | Higgins et al. |
| 5,376,088 A | 12/1994 | Glaros |
| 5,423,809 A | 6/1995 | Klicek |
| 5,540,683 A | 7/1996 | Ichikawa et al. |
| 5,613,966 A | 3/1997 | Makower et al. |
| 5,716,389 A | 2/1998 | Walinsky et al. |
| 5,836,897 A * | 11/1998 | Sakurai et al. ............... 601/2 |
| 5,949,644 A | 9/1999 | Park |
| 5,971,981 A | 10/1999 | Hill et al. |
| 6,053,886 A | 4/2000 | Holland, Jr. et al. |
| 6,228,079 B1 | 5/2001 | Koenig |
| 6,347,251 B1 | 2/2002 | Deng |
| 6,352,532 B1 | 3/2002 | Kramer et al. |
| 7,066,933 B2 | 6/2006 | Hagg |
| 7,118,564 B2 | 10/2006 | Ritchie et al. |
| 2004/0015163 A1 | 1/2004 | Buysse et al. |
| 2004/0030329 A1 | 2/2004 | Hagg |
| 2004/0230262 A1 | 11/2004 | Sartor et al. |
| 2005/0113815 A1 | 5/2005 | Ritchie et al. |
| 2006/0105603 A1 | 5/2006 | Nishio et al. |
| 2007/0038209 A1 | 2/2007 | Buysse et al. |
| 2008/0058803 A1 * | 3/2008 | Kimura ............... 606/49 |

FOREIGN PATENT DOCUMENTS

| | | |
|---|---|---|
| GB | 2 452 964 | 3/2009 |
| JP | 3-272755 | 12/1991 |
| JP | 10-085228 | 4/1998 |
| JP | 11-047148 | 2/1999 |
| JP | 11-318919 | 11/1999 |
| JP | 2001060773 | 3/2001 |
| JP | 2003174267 | 6/2003 |
| JP | 2005-024707 | 1/2005 |
| JP | 2006-62177 | 3/2006 |
| JP | 2006062177 | 9/2006 |
| JP | 2007165094 | 6/2007 |
| WO | WO 93/13718 | 7/1993 |
| WO | WO 93/22977 | 11/1993 |
| WO | WO 2006035659 | 4/2006 |
| WO | WO 2006/127629 | 11/2006 |

OTHER PUBLICATIONS

English Translation of Japanese Office Action mailed Dec. 3, 2010 in connection with corresponding Japanese Patent Application No. 2009-211615.

English Translation of Japanese Office Action mailed May 12, 2010 in connection with corresponding Japanese Patent Application No. 2009-211615.

* cited by examiner

MEDICAL TECHNOLOGY DEVICE AND MEDICAL TECHNOLOGY DEVICE ARRANGEMENT

CROSS-REFERENCE TO RELATED APPLICATIONS

This application is a divisional of U.S. application Ser. No. 12/537,319, filed Aug. 7, 2009, now abandoned, by Andreas HÖRLLE entitled MEDICAL TECHNOLOGY DEVICE AND MEDICAL TECHNOLOGY DEVICE ARRANGEMENT, which is based upon and claims the benefit of priority to German Patent Application No. 10 2008 047 339.1, filed Sep. 15, 2008, which is incorporated herein by reference in its entirety.

FIELD OF THE INVENTION

The invention concerns a medical technology device for treatment of the human or animal body, comprising at least one electrical plug connector which is adapted to be connected to a complementary counterpart plug connector of a further medical technology device and which in an active position is arranged projecting upwardly at the top side of the device.

BACKGROUND OF THE INVENTION

For many years now the many different possible uses of medical technology have led to a large number of specialised end devices such as for example high frequency generators, ultrasound generators or argon plasma units. In order always to provide the physician with an optimum device for various uses, multifunctional devices or device arrangements have been developed. In the simplest case those devices or device arrangements are afforded by electrically and mechanically connecting two or more devices. A known example is connecting an argon plasma unit to a high frequency generator, referred to for brevity as an HF generator. In that case a high frequency current is passed into the argon plasma unit by way of a plug connection to be able to connect the argon plasma/HF manual instrument to the argon plasma unit.

The cable connection for transmission of the HF signal between the devices should be kept as short as possible. With increasing length, when carrying high frequency ac voltages, the electrical leakage currents or stray currents increase and electromagnetic compatibility decreases. Preferably therefore the HF plug connection between the devices which are usually disposed in mutually superposed relationship is arranged in the proximity of the output jacks of the manual instruments.

The problem which arises with all known device arrangements is that the devices cannot be used, or at least cannot both be used, as an individual device. At least in one of the devices, electrical contacts are exposed in the uncoupled condition so that existing medical device safety standards, for example in relation to protection from spray water, cannot be observed. In addition the uncoupled individual devices generally do not meet the aesthetic demands which are usual nowadays.

SUMMARY OF THE INVENTION

Therefore the object of the present invention is to provide a medical technology device which can be used both as an individual device and also in conjunction with a second device as a device arrangement and in that respect satisfies existing safety and aesthetic demands.

According to the invention that object is attained by the above-mentioned medical technology device in that the plug connector is adapted to be movable from the active position into a passive position, wherein in the passive position the plug connector is removed from the top side of the device and the top side is closed in substantially fluid-tight relationship.

The solution according to the invention has the advantage that the medical technology device can be very easily converted between an individual operating mode and a combination operating mode. The possible uses of the device according to the invention are thus considerably enhanced because it can now be used both as an individual device and also as a combination device.

The solution according to the invention can be supplemented by further advantageous configurations. Some such configurations are described hereinafter.

Thus the medical technology device can have at least one lift unit by which the plug connector is movably connected to the rest of the device. That has the advantage that the plug connector and therewith the medical technology device can be particularly easily and quickly converted between the active and the passive positions. In particular the lift unit can have a prismatic joint, by means of which the plug connector is movable substantially linearly from the active position into the passive position. One or more cables connected to electric contacts of the plug connector lead to the plug connector. It has been found that the linear movement of the prismatic joint is particularly well suited for carefully passing the cable to the plug connector. It will be appreciated that alternatively the lift unit can also have a rotary joint coupling or any other form of joint coupling.

Embodiments with a connecting wire or chain or also the cable as a connecting element are also possible.

In order in a simple manner to ensure protection from spray or splash water when the device is used as an individual device, the device can include at least one cover means which closes the top side of the device in the passive position in substantially fluid-tight relationship. In addition the plug connector can be connected to the cover means and arranged in the interior of the device in the passive position. Thus the cover means, for example a cover plate, serves at the same time as a holder for the plug connector.

In a further advantageous configuration the device can have at least one drive means which urges the plug connector from the passive position in the direction of the active position. That has the advantage that the plug connector automatically moves from the passive position which involves poor access, in the interior of the medical technology device, into the active position. By way of example a spring element such as a compression coil spring can be used as the drive means.

The invention further includes a medical technology device arrangement for treatment of the human or animal body, comprising at least two medical technology devices which are electrically and mechanically connected together by way of a plug connector arrangement, wherein the plug connector arrangement includes a plug connector connected to the first device and a counterpart plug connector which is connected to the second device and which is of a complementary configuration to the plug connector. In order to be able to use both devices separately the first medical technology device is designed in accordance with one of the foregoing embodiments.

In a particularly advantageous configuration of the device arrangement the first device can be an ultrasound generator and the second device can be an HF generator. There are many uses for ultrasound generators and HF generators as individual devices and also as a combination device so that this affords very many possible uses for the device arrangement.

To connect combined ultrasound-HF instruments, the device arrangement can be so adapted that in operation both a high frequency current signal and also a signal for an ultrasound instrument can be taken off simultaneously at the ultrasound generator. Combined ultrasound-HF instruments produce for example ultrasound energy for tissue cutting and use HF energy for coagulating the tissue prior to cutting.

The invention is described in greater detail hereinafter by means of embodiments by way of example illustrated in the drawings. The different features can be combined together as desired, as also in the above-described embodiments.

DETAILED DESCRIPTION OF THE INVENTION

Figure 1:
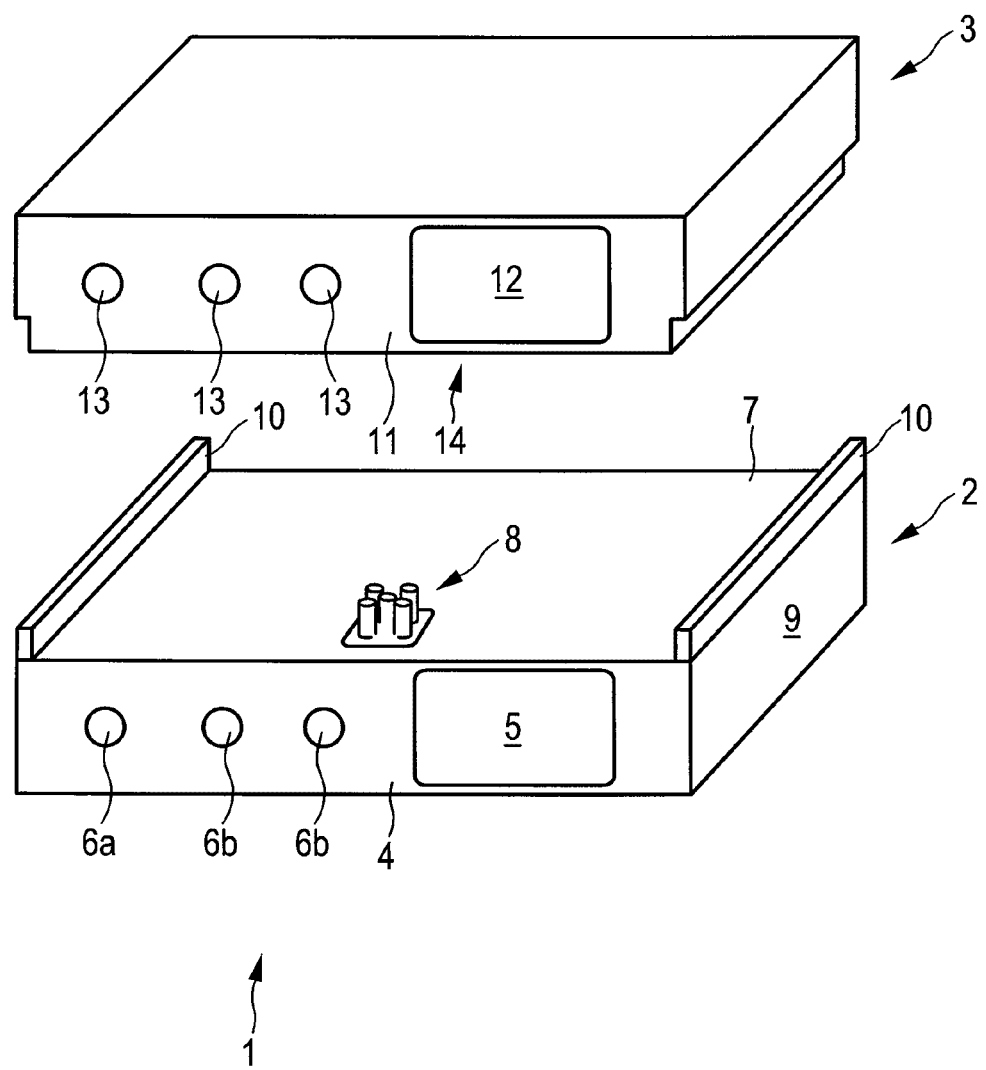
FIG. 1 shows a diagrammatic view of an embodiment by way of example of a device arrangement according to the invention.

A medical technology device arrangement 1 in FIG. 1 includes an ultrasound generator 2 and an HF generator 3.

At the front side 4 the ultrasound generator 2 has a touch screen operating panel 5 and output jacks 6a, 6b. On its housing cover 7 at the top side, in the proximity of the front side 4, the ultrasound generator 2 has an upwardly projecting plug connector 8. Two holding bars 10 are disposed also projecting upwardly but laterally as a prolongation of the side walls 9.

The output jacks 6a are adapted for the connection of surgical ultrasound instruments and the output jacks 6b are adapted for the connection of combined HF/ultrasound instruments. Combined HF/ultrasound instruments can produce an ultrasound signal and in addition have one or more electrodes for the delivery of HF energy to the tissue to be treated. As the ultrasound generator 2 itself cannot generate any HF energy for the combined HF/ultrasound instruments, it is passed by way of the plug connector 8 from the HF generator 3 into the ultrasound generator 2, as described in greater detail hereinafter with reference to FIGS. 2 through 11. By way of the touch screen operating panel 5 the user can perform the necessary settings both for the individual mode of operation and also the combination mode of operation. The holding bars 10 arrest the ultrasound generator 2 in relation to the HF generator 3 in the combined state and can be fixed to the generators 2, 3 with fixing means such as for example screws. Alternatively the holding bars 10 for example can also be arranged as a prolongation of the rear wall.

Figure 4:
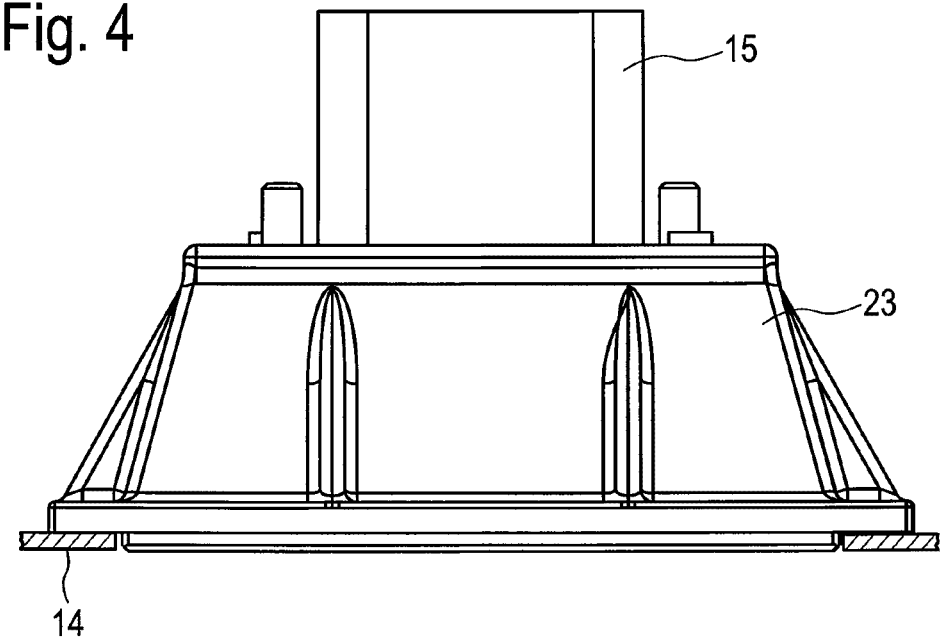
FIG. 4 shows a diagrammatic view of an embodiment by way of example of a counterpart plug of the device arrangement of FIG. 1.

Similarly as in the case of the ultrasound generator 2, arranged at the front side 11 of the HF generator 3 there are also a touch screen operating panel 12 and various output jacks 13. Provided in the bottom 14 of the housing of the HF generator 3, though not visible in FIG. 1, is a counterpart plug connector 15 of a complementary configuration to the plug connector 8 of the ultrasound generator 2. The configuration of the counterpart plug connector 15 is shown in FIG. 4 and is described in greater detail hereinafter.

Figure 12:
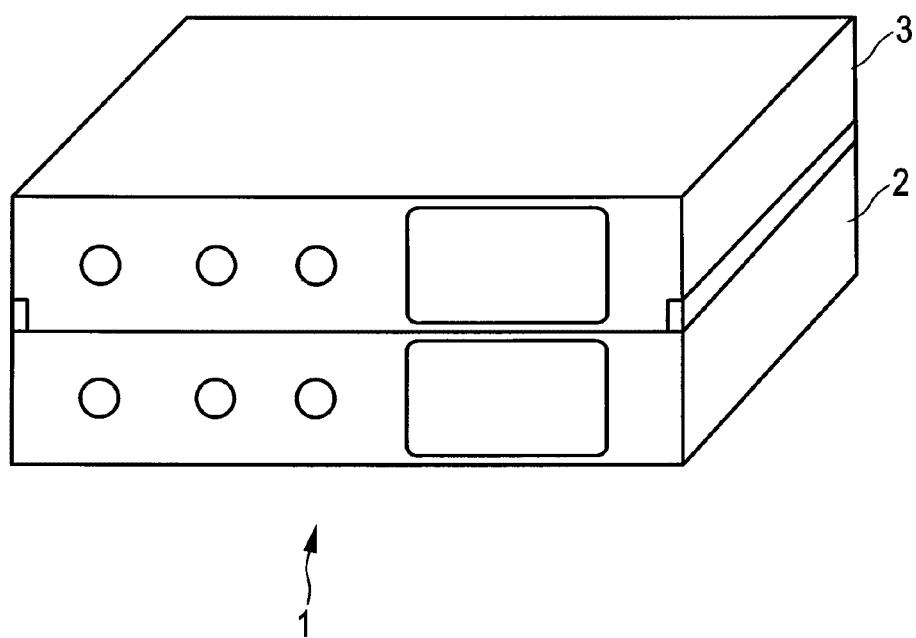
FIG. 12 shows a diagrammatic view of the device arrangement according to the invention as shown in FIG. 1 with connected devices.

FIG. 1 shows the ultrasound generator 2 and the HF generator 3 in a position before they are connected. FIG. 12 shows the device arrangement 1 with connected generators 2, 3, as they are disposed in the combination mode of operation. It will be appreciated that other medical technology devices can also be connected with the plug connector according to the invention.

In the combination mode of operation the HF generator 3 transmits HF energy by way of the counterpart plug connector 15 coupled to the plug connector 8, to the ultrasound generator 2. Otherwise the HF generator 3 also has all features of a commercially available HF generator, which will not be discussed in greater detail here.

Figure 2:
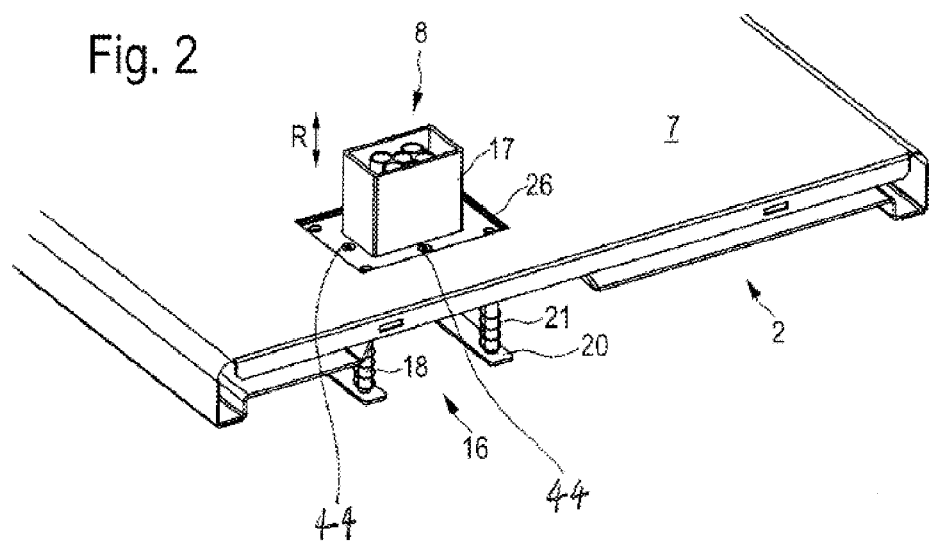
FIG. 2 shows a diagrammatic view of a first embodiment by way of example of a medical technology device according to the invention from above.
Figure 3:
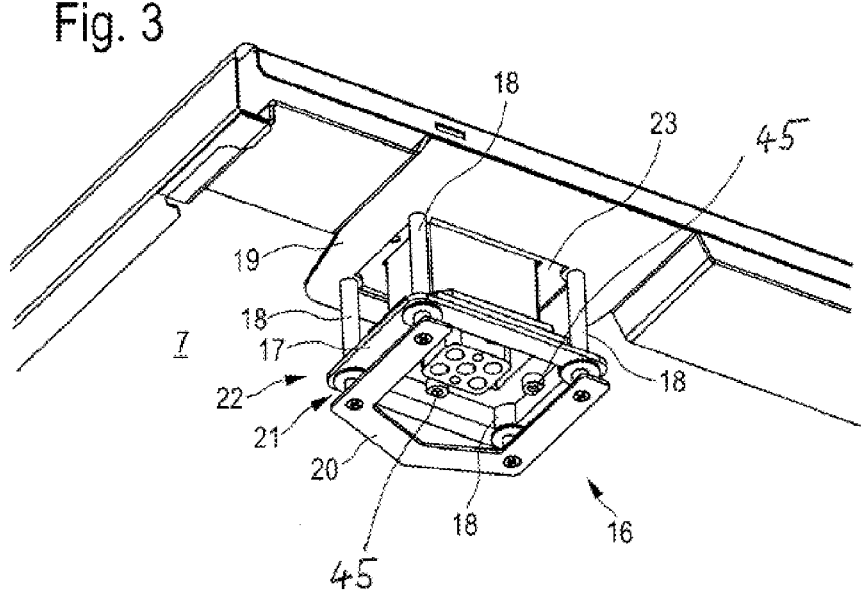
FIG. 3 shows a diagrammatic view of the medical technology device of FIG. 2 from below.

Reference is now made to FIGS. 2 and 3 to describe in greater detail a first embodiment of the medical technology device 2 according to the invention with the plug connector 8. For the sake of enhanced clarity the parts which are not relevant to the plug connector 8, such as for example the front side, of the ultrasound generator 2, have been omitted from FIGS. 2 and 3.

FIG. 2 shows the plug connector 8 in an active position in which the plug connector 8 is extended and projects upwardly beyond the housing cover 7. FIG. 3 shows the plug connector 8 in a passive position in which it is retracted into the interior of the ultrasound generator 2 so that the plug connector does not project above the housing cover 7.

In the embodiment of FIGS. 2 and 3 the plug connector 8 is connected to a lift unit 16 fixed to the housing cover 7. The lift unit 16 with the plug connector 8 is arranged in a rectangular opening 26 in the housing cover 7. In FIGS. 2 and 3 the lift unit 16 is screwed to the housing cover 7 and the plug connector 8 is screwed to the lift unit 16. Alternatively however they can also be welded, riveted, glued or fixed in some other fashion. The lift unit 16 has a rectangular flange frame 17 to which the plug connector 8 is connected. The flange frame 17 is movably coupled to a linear guide in the form of four guide rods 18. The guide rods 18 which are of equal length and which extend in mutually parallel relationship are respectively fixed relative to each other at the ends. The upper ends are connected to the housing cover 7 by way of a reinforcing plate 19. The lower ends are connected to a substantially U-shaped fixing plate 20. Compression coil springs 21 are arranged around the guide rods 18, between the flange frame 17 and the fixing plate 20.

The plug connector 8 is arranged linearly movably by the lift unit 16. The flange frame 17, with the guide rods 18, forms a prismatic joint 22, by means of which the plug connector 8 is movable substantially linearly between the active position in FIG. 2 into the passive position in FIG. 3 in a direction of movement R. The direction of movement R extends substantially at a right angle to the plane of the housing cover 7. To reduce friction between the guide rods 18 and the flange frame 17 anti-friction bushes for example can be fitted into the flange frame 17.

The flange frame 17 is of a substantially two-stage structure and has a wide lower flange and a narrow upper flange. The wide lower flange is connected to the guide rods 18 and is always disposed in the interior of the ultrasound generator 2. The narrow upper flange is connected to the plug connector and projects above the housing cover 7 in the active position. In the center the flange frame 17 has a cable opening through which the cables (not shown) can be passed to the plug connector.

The lift unit 16 can be arrested in the active position in FIG. 2 to prevent unwanted lowering movement of the plug connector 8, for example when the two generators 2, 3 are being fitted together. The arresting action can be effected for example by screwing or however also by latching.

The compression coil springs 21 are provided as a drive unit which always urges the lift unit 16 and therewith the plug connector 8 in the direction of the active position. It is thus particularly easy for the operator to move the plug connector 8 from the inwardly disposed passive position in which access to the plug connector 8 is difficult, into the active position.

The ultrasound generator 2 further includes a cover portion 23 which closes the housing cover 7 in substantially fluid-tight relationship in the passive position. The cover portion 23 is produced for example from a metal plate screwed to the housing cover 7. To enhance the sealing effect a seal can be arranged between the cover portion 23 and the housing cover 7. The cover portion 23 can also serve at the same time as an arresting means which holds the lift unit 16 in the passive position. It will be appreciated that alternatively a latching means or similar can also be provided as a means for arresting the lift unit 16 in the passive position.

FIG. 4 shows the counterpart plug connector 15 fitted in the HF generator 3. The counterpart plug connector 15 is connected to a funnel-shaped holder 44 fixed to the housing bottom 14. The funnel-shaped configuration of the holder 44 facilitates positioning of the plug connector 8 relative to the counterpart plug connector 15 when coupling the two generators 2, 3. The counterpart plug connector 15 with the holder 44 remains unchanged when separating or connecting the two generators 2, 3. The electrical contacts (not shown) in the counterpart plug connector 15 are so arranged that they cannot be touched by the operator when the devices 2, 3 are separated.

Figure 5:
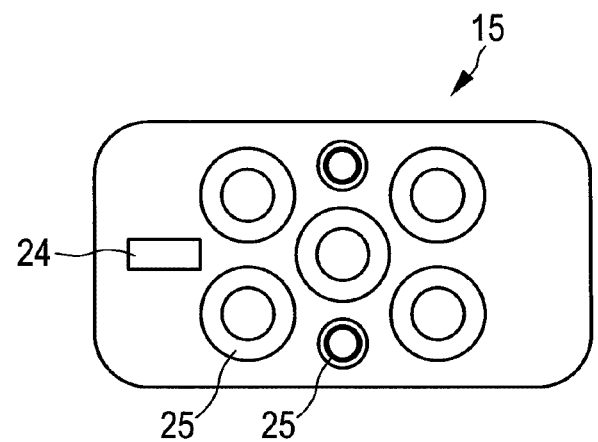
FIG. 5 shows a diagrammatic view of the counterpart plug connector of FIG. 4 from above.

FIG. 5 shows a view of the counterpart plug connector 15 from below. The counterpart plug connector 15 includes a mechanical orientation projection 24 to prevent incorrect insertion, and bores for fixing screws. In addition it has a plurality of contact pins 25 for transmission of various electrical signals such as for example HF signals for monopolar and bipolar applications and signals for connection recognition. The counterpart plug connector 15 is of a complementary configuration to the plug connector 8.

Figure 6:
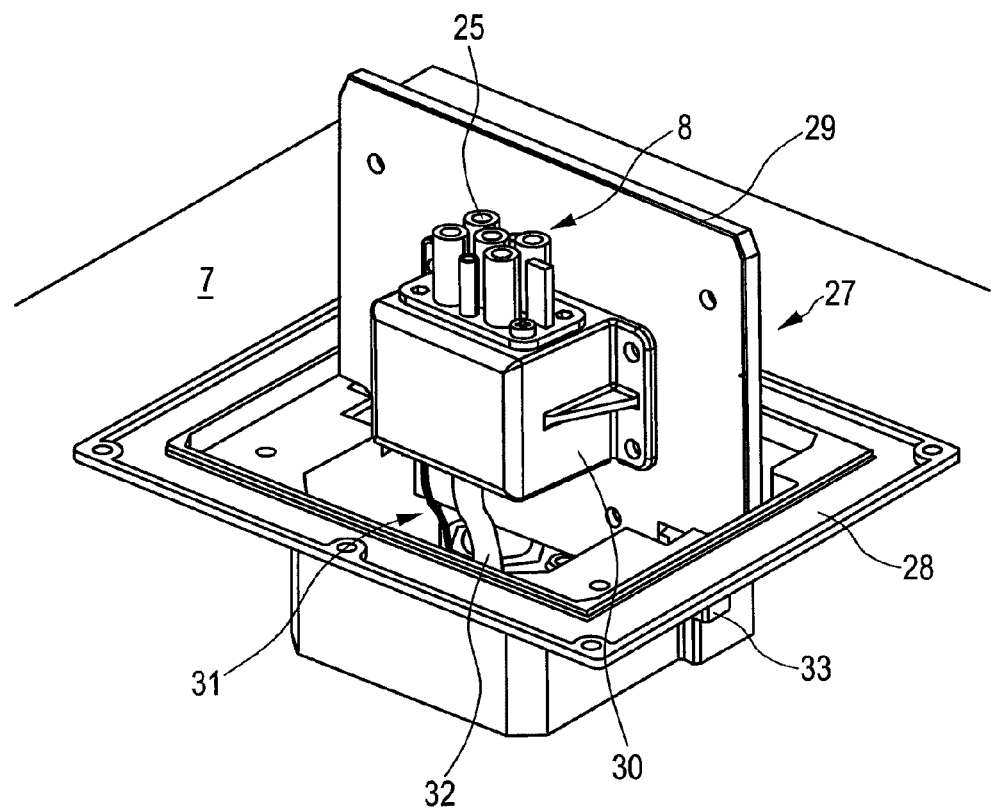
FIG. 6 shows a diagrammatic view of a further embodiment by way of example of a medical technology device according to the invention in an active position.
Figure 7:
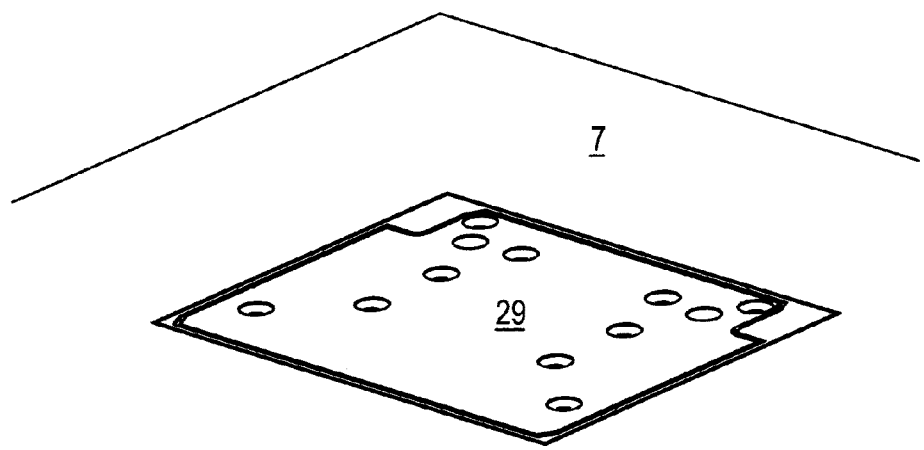
FIG. 7 shows a diagrammatic view of the medical technology device of FIG. 6 in a passive position.

A further embodiment of the device 2 according to the invention with an alternative lift unit 27 is shown in FIGS. 6 and 7 and described hereinafter. For the sake of brevity only the differences in relation to the above-described embodiment are considered here. FIG. 6 shows the housing cover 7 transparent, for the sake of clarity. FIG. 6 shows the plug connector 8 with an alternative lift unit 27 in the active position, while FIG. 7 shows them in the passive position.

The lift unit 27 in FIGS. 6 and 7 includes a receiving shell 28, a turning plate 29 and an intermediate portion 30 to which the plug connector 8 is fixed. The lift unit 27 also has a connecting wire 31 as a mechanical movable connection between the turning plate 29 and the receiving shell 28. An electrical connecting cable 32 connects the contacts (not shown) of the plug connector 8 to the corresponding contacts (not shown) in the interior of the ultrasound generator 2. The connecting cable 32 is longer than the connecting wire 31 to avoid tensile forces on the connecting cable 32. The receiving shell 28 has a receiving depression 33 in which the turning plate 29 extends in the active position in FIG. 6. The contact pins 25 of the plug connector 8 extend substantially parallel to the flat turning plate 29 which extends substantially at a right angle to the housing cover 7 in the receiving depression 33. Thus in the active position the plug connector 8 projects above the housing cover 7.

To move the plug connector 8 into the passive position the turning plate 29 is removed from the receiving depression 33 and placed on the receiving shell 28 in a position of being turned through 90° so that the plug connector 8 is in the interior of the receiving depression 33. The passive position is shown in FIG. 7 with a view on to the ultrasound generator 2 from above. The turning plate 29 can be fixed in the passive position by fixing means such as for example screws (not shown).

Figure 8:
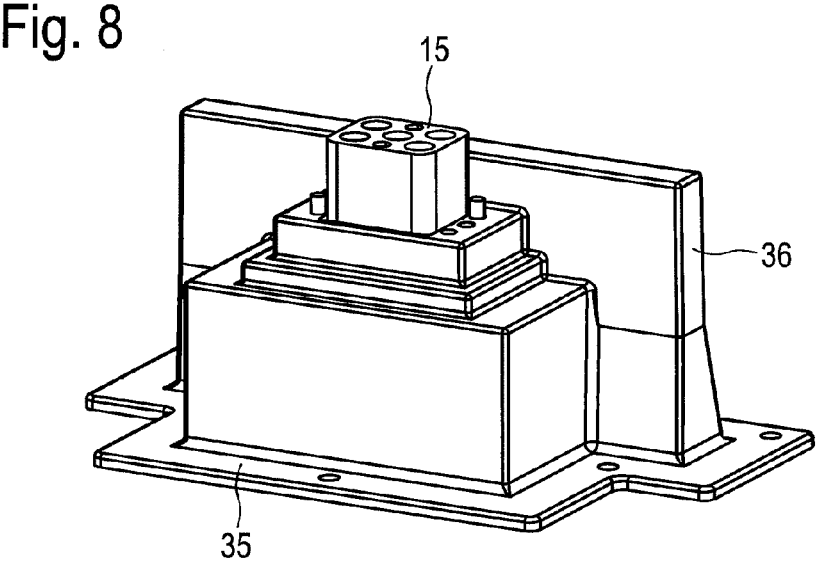
FIG. 8 shows a diagrammatic view of an embodiment by way of example of a counterpart plug for a device arrangement with the device of FIGS. 6 and 7.

FIG. 8 shows a holder 35 for the counterpart plug connector 15, that is suited for the embodiment of FIGS. 6 and 7. Unlike the holder 44 in FIG. 4 the holder 35 has a shaped depression 36 into which the turning plate 29 can engage from below when the devices 2, 3 are connected.

Figure 9:
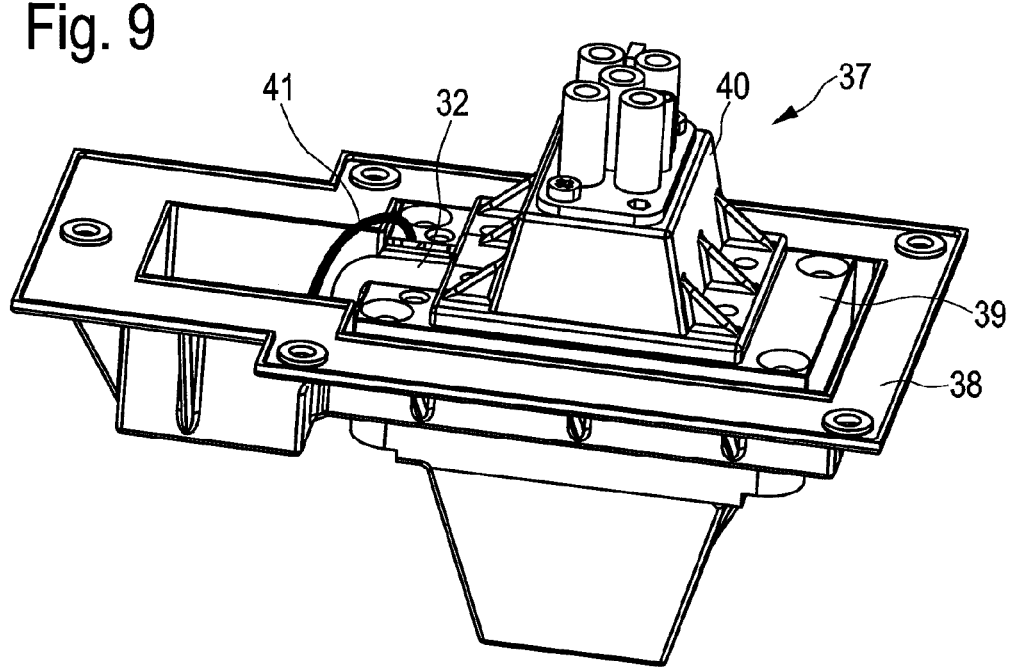
FIG. 9 shows a diagrammatic view of a further embodiment by way of example of a medical technology device according to the invention in an active position.
Figure 10:
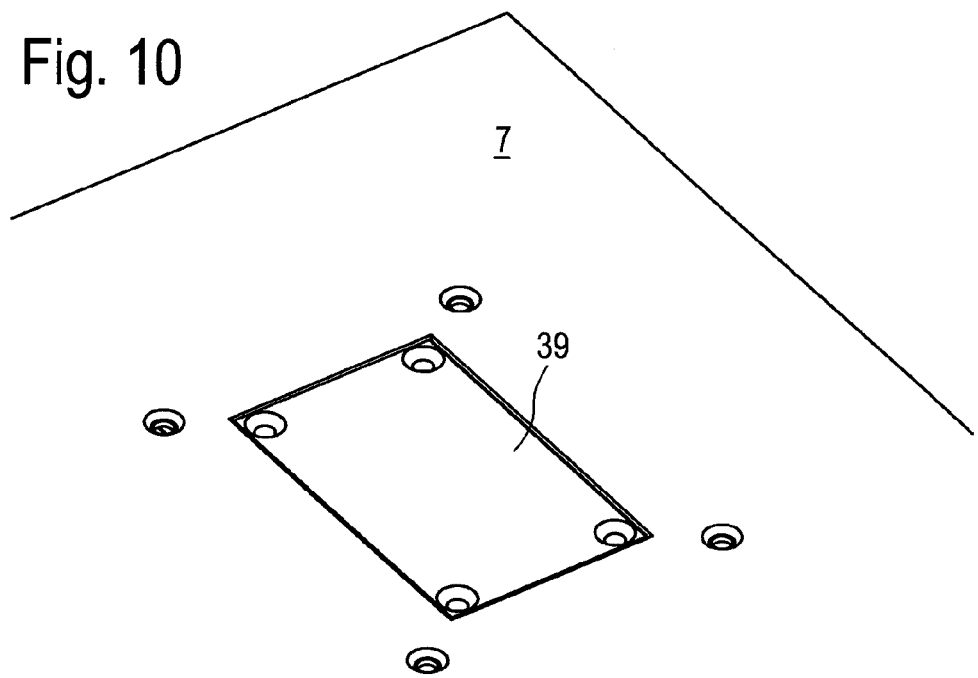
FIG. 10 shows a diagrammatic view of the medical technology device of FIG. 9 in a passive position.

A further embodiment of the device 2 according to the invention with an alternative lift unit 37 is shown in FIGS. 9 and 10 and described hereinafter. For the sake of brevity only the differences in relation to the above-described embodiments are considered here. FIG. 9 does not show the housing cover 7 of the ultrasound generator 2. FIG. 9 shows the plug connector 8 with an alternative lift unit 37 in the active position while FIG. 10 shows them in the passive position.

Like the embodiment of FIG. 6 the lift unit 37 of the embodiment of FIGS. 9 and 10 also includes a receiving shell 38, a turning plate 39 and an intermediate portion 40 to which the plug connector 8 is fixed. A connecting wire 41 in this case also connects the turning plate 39 to the receiving shell 38. It will be noted however that the turning plate 39 has to be rotated through 180° to move the lift unit 37 from the active position in FIG. 9 into the passive position in FIG. 10. The turning plate 39 can also be secured in the passive position in FIG. 10 for example with fixing screws (not shown). For this embodiment it is also possible to use the counterpart plug connector 15 with the holder 23 from FIG. 4.

Figure 11:
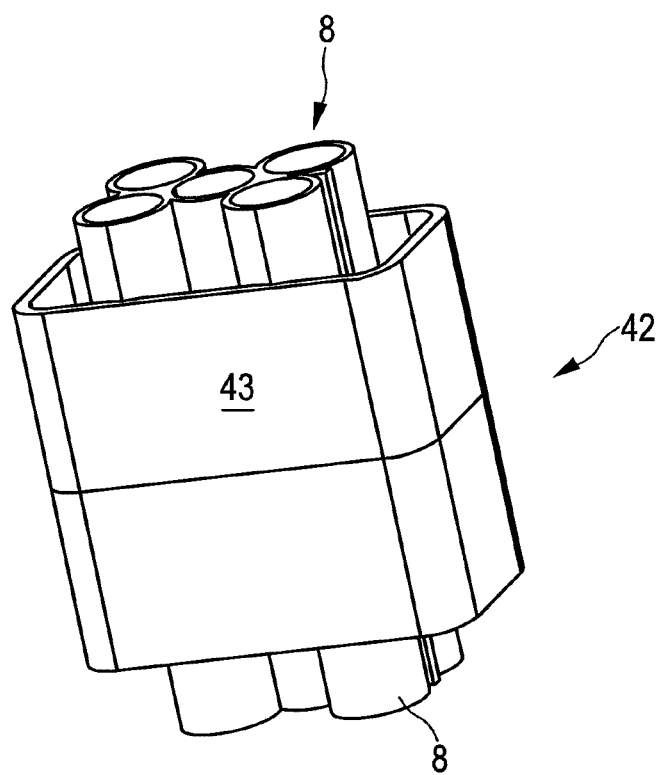
FIG. 11 shows a diagrammatic view of a plug connector of a further embodiment by way of example of a medical technology device according to the invention.

A further embodiment of the invention is shown in FIG. 11. FIG. 11 shows a double plug connector 42 in which a plug connector 8 is arranged at each end. The plug connectors 8 are fixed in a housing 43 and the contacts thereof (not shown) are respectively connected together in the interior of the housing. For use of the double plug connector 42 both the ultrasound generator 2 and also the HF generator 3 are equipped with the holder 44 and the counterpart plug connector 15 of FIG. 4. In the active position the double plug connector 42 is fitted on to the counterpart plug connector 15 of the ultrasound generator 2. Thus the ultrasound generator 2 can be connected to the HF generator 3. For the passive position the double plug connector 42 is removed and a cover plate closes the housing cover 7 in fluid-tight relationship.

The invention claimed is:

1. A medical technology device arrangement for treatment of a human or an animal body, comprising:
   at least two medical technology devices which are electrically and mechanically connected together by way of a plug connector arrangement, the at least two medical technology devices including first and second medical technology devices, each having a respective bottom wall and a respective top wall, the top wall of the first medical technology device is structurally configured to support directly thereon the second medical technology device in a state when the first and second medical technology devices are electrically coupled via said plug connector arrangement,
   the plug connector arrangement comprises an electrical plug connector provided at the top wall of the first medical technology device and a counterpart electrical plug connector which is arranged in the bottom wall of the second medical technology device, the bottom wall of the second medical technology device being configured to enable its stacking on the top wall of the first medical device, and the counterpart electrical plug connector being of a complementary configuration relative to the electrical plug connector and being configured to be connected thereto, and
   wherein the electrical plug connector is configured to be in an active position for connection to the counterpart electrical plug by being arranged to be aligned with and to project in an upward direction from the top wall of the first medical technology device, and configured to be movable from the active position into a passive position, wherein, in the passive position, the electrical plug connector is configured to be removed from the top wall of the first medical technology device and the top wall is configured to be closed in a substantially fluid-tight condition, and
   wherein the electrical plug connector in its active position is arranged so as to project into the counterpart electrical plug connector for electrically coupling the two medical technology devices when the second of the medical technology devices is stacked directly upon the first medical technology device.

2. The medical technology device arrangement according to claim 1, wherein the first medical technology device is an ultrasound generator and the second medical technology device is a high-frequency (HF) generator.

3. The medical technology device arrangement according to claim 2, wherein the medical technology device arrangement is so configured that in operation a high frequency current signal and a signal for an ultrasound instrument can be taken off are simultaneously provided at the ultrasound generator.

4. The medical technology device arrangement according to claim 1, wherein the first medical technology device comprises a lift unit positioned to movably connect the electrical plug connector to the second medical technology device, and the lift unit is configured to be able to be immovably arrested in the active position to thereby prevent unwanted lowering movement of the electrical plug connector, wherein the lift unit comprises a prismatic joint configured to allow the electrical plug connector to move from the active position into the passive position and from the passive position to the active position with such movement being substantially linearly in a direction in which the counterpart electrical plug connector is inserted into the electrical plug connector that is moveably connected to the lift unit.

5. The medical technology device arrangement according to claim 4, wherein the first medical technology device is an ultrasound generator and the second medical technology device is an HF generator.

6. The medical technology device arrangement according to claim 5, wherein the medical technology device arrangement is so configured that a high frequency current signal and a signal for an ultrasound instrument are simultaneously provided at the ultrasound generator.

\* \* \* \* \*